(12) United States Patent
Rasmussen et al.

(10) Patent No.: US 7,806,837 B2
(45) Date of Patent: Oct. 5, 2010

(54) GUIDE WIRE FOR CATHETER

(75) Inventors: Erik E. Rasmussen, Slagelse (DK); Per Hendriksen, Herlufmagle (DK); Steen Aggerhold, St. Heddine (DK)

(73) Assignees: William Cook Europe ApS, Bjaeverskov (DK); Cook Incorporated, Bloomington, IN (US)

( * ) Notice: Subject to any disclaimer, the term of this patent is extended or adjusted under 35 U.S.C. 154(b) by 279 days.

(21) Appl. No.: 11/983,145

(22) Filed: Nov. 7, 2007

(65) Prior Publication Data

US 2009/0118645 A1    May 7, 2009

(51) Int. Cl.
*A61B 5/00* (2006.01)
*A61M 25/00* (2006.01)

(52) U.S. Cl. ...................................... 600/585

(58) Field of Classification Search ................ 600/585, 600/115, 104; 29/428
See application file for complete search history.

(56) References Cited

U.S. PATENT DOCUMENTS

| | | | |
|---|---|---|---|
| 5,253,653 A | 10/1993 | Daigle et al. | |
| 5,606,981 A | 3/1997 | Tartacower et al. | |
| 5,830,155 A | 11/1998 | Frechette et al. | |
| 5,836,892 A | 11/1998 | Lorenzo | |
| 6,019,737 A | 2/2000 | Murata | |
| 6,612,998 B2 | 9/2003 | Gosiengfiao et al. | |
| 6,620,114 B2 | 9/2003 | Vrba et al. | |
| 6,636,758 B2 | 10/2003 | Sanchez et al. | |
| 7,278,974 B2 | 10/2007 | Kato | |
| 7,303,798 B2 | 12/2007 | Bavaro et al. | |
| 7,455,646 B2 | 11/2008 | Richardson et al. | |
| 2003/0208142 A1 | 11/2003 | Boudewijn et al. | |
| 2004/0133129 A1* | 7/2004 | Harari et al. | 600/585 |
| 2004/0181174 A2 | 9/2004 | Davis et al. | |
| 2005/0148901 A1* | 7/2005 | Parins et al. | 600/585 |
| 2005/0255317 A1 | 11/2005 | Bavaro et al. | |
| 2005/0267385 A1 | 12/2005 | Hoffman et al. | |
| 2007/0249964 A1* | 10/2007 | Richardson et al. | 600/585 |
| 2008/0103361 A1* | 5/2008 | Makower et al. | 600/115 |

* cited by examiner

*Primary Examiner*—Max Hindenburg
*Assistant Examiner*—Brian Szmal
(74) *Attorney, Agent, or Firm*—Richard J. Godlewski; Kevin L. Leffel; Charles W. Agnew

(57) ABSTRACT

A guide wire (10) for a catheter carrying an implant includes alternating radio-opaque zones (16) and radio-transparent zones (18) formed from a granular material at a portion of the guide wire (10) just proximal to a flexible tip (12). The granular material is compressed within a sheath formed by the guide wire (10) and held in place by a bung (11). By regularly spacing the radio-opaque zones (16), the guide wire (10) enables in situ measurements to be taken within a patient's vasculature. The use of granular material to form the radio-opaque zones (16) and the radio-transparent zones (18) provides rigidity to the portion of the guide wire (10) proximal to the tip (12).

11 Claims, 3 Drawing Sheets

GUIDE WIRE FOR CATHETER

TECHNICAL FIELD

The present invention relates to a guide wire for a catheter and to a delivery or treatment system including a guide wire.

BACKGROUND OF THE INVENTION

A typical endoluminal deployment system includes an inner catheter or cannula which may also be arranged as a pusher and/or dilator (hereinafter referred to as an inner catheter or catheter element) and a sheath covering the inner catheter. An implant or prosthesis is carried on the inner catheter and is fixed thereto by means of the covering sheath and with or without one or more restraining wires or any of a number of other known retention systems.

The implant or prosthesis might be a stent, a stent graft, a filter, an occlusion device or any other implantable device of such a nature.

Once the distal end of the catheter has been positioned inside a patient, typically at the site of the patient's vasculature to be treated, the device is released and deployed in the desired position. The deployment operation involves retracting the covering sheath so as to expose the device to be implanted, which device is then deployed, either by self-expansion or by means of an expansion device such as an inflatable balloon. In the case where the device is also held by restraining wires, these are withdrawn, typically after retraction of the sheath. Restraining wires may or may not be used in such apparatus, generally dependent upon the nature of the device to be deployed, size restrictions and the particular medical application or intervention procedure.

In order to position a catheter at the site of the patient's vasculature to be treated, a guide wire is first inserted through the vasculature, for example, via the femoral artery. Once the guide wire is in position, a dimensioning catheter is passed over the guide wire to the site of treatment. The dimensioning catheter is provided with a plurality of gold marker bands and is used to determine the length of the vasculature that requires treatment. Once this has been determined, the dimensioning catheter is removed. The appropriate implant is then selected and delivered using a second catheter that is passed over the same guide wire. Typically, the positioning of the implant is achieved with X-ray analysis during the procedure.

SUMMARY OF THE INVENTION

The present invention seeks to provide an improved guide wire for a catheter.

According to an aspect of the present invention, there is provided a guide wire for a catheter, said guide wire having a longitudinal axis, said guide wire including a sheath, a plurality of marker elements housed within said sheath and regularly spaced along said longitudinal axis, said markers having different radio-opacities.

This arrangement allows a guide wire to have a dual function. Not only does it guide a catheter to a site of a patient's vasculature, it also provides markers to assist in treatment or deployment of an implant. The guide wire avoids the need for an additional dimensioning catheter to be used.

The marker elements may be formed by a granular material within the sheath. The granular material preferably includes tungsten powder and sand. Use of a granular material provides a relatively rigid portion for the guide wire.

The granular material is preferably held in place by a bung. This holds the granular material and thus the marker elements in place.

Preferably at least two radio-opaque marker elements are provided. The two radio-opaque marker elements are preferably separated by a known distance to allow a measurement of a lesion in vasculature to be taken without the need for a separate dimensioning catheter.

Advantageously, the known distance is approximately 1 cm and the at least two radio-opaque marker elements are approximately 1 cm in length. This allows measurements to the nearest centimeter to be taken.

According to another aspect of the present invention, there is provided a delivery or treatment system including a guide wire as specified herein.

In the case of a delivery system, this is preferably of a type able to carry and deliver a stent, a stent graft, a vena cava filter, an occlusion device or any other implant or prosthesis.

According to another aspect of the present invention, there is provided a guide wire for a catheter, said guide wire having a longitudinal axis, said guide wire including a sheath containing a granular material, wherein said granular material forms at least two radio-opaque markers, said markers being regularly spaced along said longitudinal axis, said markers alternating with substantially radio-transparent bands of granular material, the granular material being held in place by a bung.

BRIEF DESCRIPTION OF THE DRAWING

Embodiments of the present invention are described below, by way only, with reference to the accompanying drawing, in which.

DETAILED DESCRIPTION

It is to be understood that the Figures are schematic and do not show the various components in their actual scale. In many instances, the Figures show scaled up components to assist the reader.

In this description, when referring to a deployment or treatment assembly, the term distal is used to refer to an end of a component which in use is furthest from the surgeon during the medical procedure, including within a patient. The term proximal is used to refer to an end of a component closest to the surgeon and in practice in or adjacent an external manipulation part of the deployment of treatment apparatus.

On the other hand, when referring to an implant such as a stent or stent graft, the term proximal refers to a location which in use is closest to the patient's heart, in the case of a vascular implant, and the term distal refers to a location furthest from the patient's heart.

In the applicant's delivery system for its Zilver™ stent, a delivery assembly includes an introducer catheter 32. Housed within the introducer catheter 32 is an inner catheter 36 which carries a stent 30 and which is provided at its distal end with a flexible introducer tip 12.

The stent may be a Zilver™ biliary stent obtainable from the applicant. The introducer catheter 32 overlies and acts as a holding sheath for the stent 30. The inner catheter 36 has a bore passing therethrough for the introduction of a guide wire to enable positioning of the implant at the site of treatment.

Figure 1:
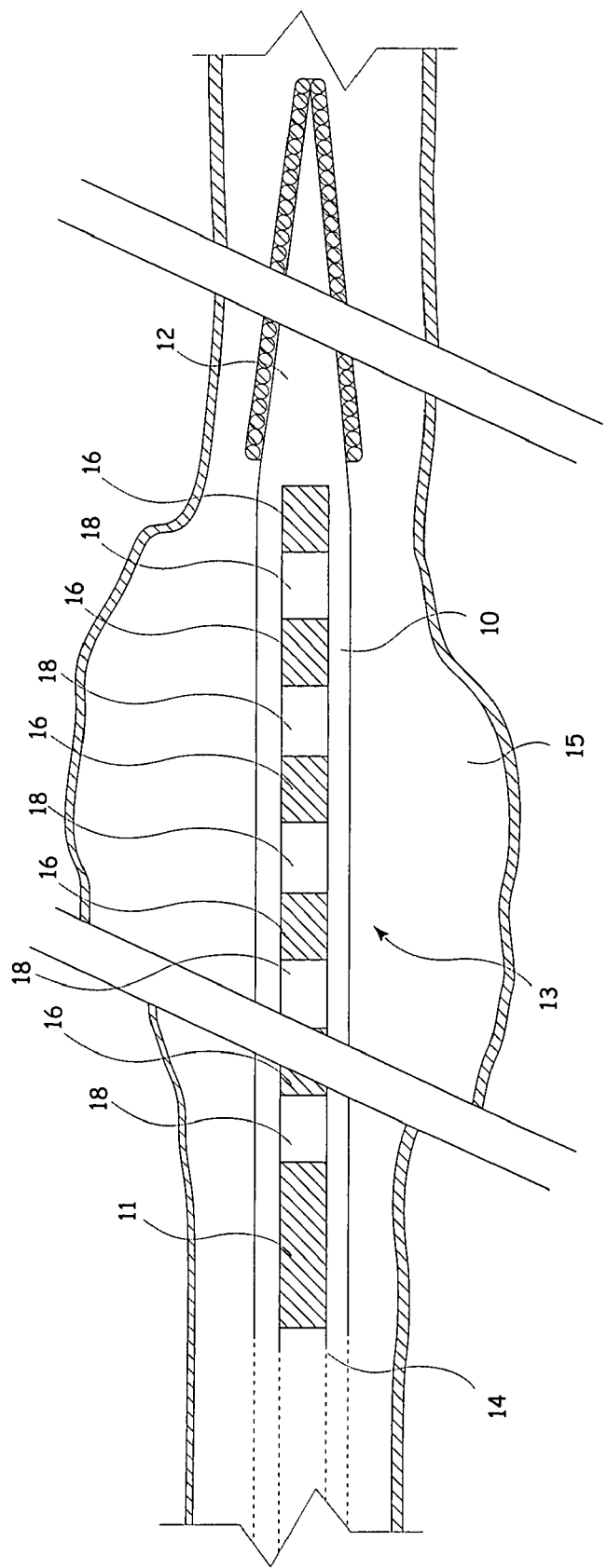
FIG. 1 is a schematic drawing of an embodiment of a guide wire.

FIG. 1 shows a drawing of a guide wire 10 in accordance with a preferred embodiment of the present invention. The guide wire 10 includes a flexible coil-wrapped tip 12 of conventional form. This is approximately 15 cm in length. Immediately proximal the tip 12 is a dimensioning portion 13 that is approximately 25 cm in length.

The guide wire 10 has a sheath 14 of non-conformal material such as stainless steel. The sheath 14, at the dimensioning portion 13, is filled with alternating sections 16, 18 of volumes of granular material having differing radio-opacities. These sections of granular material cause the dimensioning portion 13 to include alternating radio-opaque zones 16 and radio-transparent zones 18. Each zone 16, 18 is preferably 1 cm in length. The skilled person would appreciate how much of a particular granular material would be necessary in a given sheath size to provide a zone 16, 18 of the desired length. The granular material is preferably as dense as possible with minimal space between grains.

Any suitable materials can be used for the granular sections 16, 18 as long as they have readily discernible different radio-opacities. The radio-opaque zones 16 should include a high density material in powder form, for example, tungsten, gold or platinum. The radio-transparent zones 18 may include a fine sand, quartz or a stiff plastic in powder form. The grains are preferably as fine as possible and preferably pre-treated so that they are dry and not sticky.

Immediately proximal the dimensioning portion 13 of the guide wire 10 is a bung 11, preferably formed of the same material as the sheath 14. The bung 11 is used to enclose the granular material 16, 18 in the sheath 14 and to hold it in place and to prevent movement thereof. This is typically achieved by hammering the bung into the sheath 14. The granular material 16, 18 may be held in compression by the bung 11.

The alternating radio-opaque zones 16 and radio-transparent zones 18 enable an in situ measurement of the area of the patient's vasculature to be measured, and thus enable an implant of suitable size to be selected by the surgeon or clinician.

Figure 2:
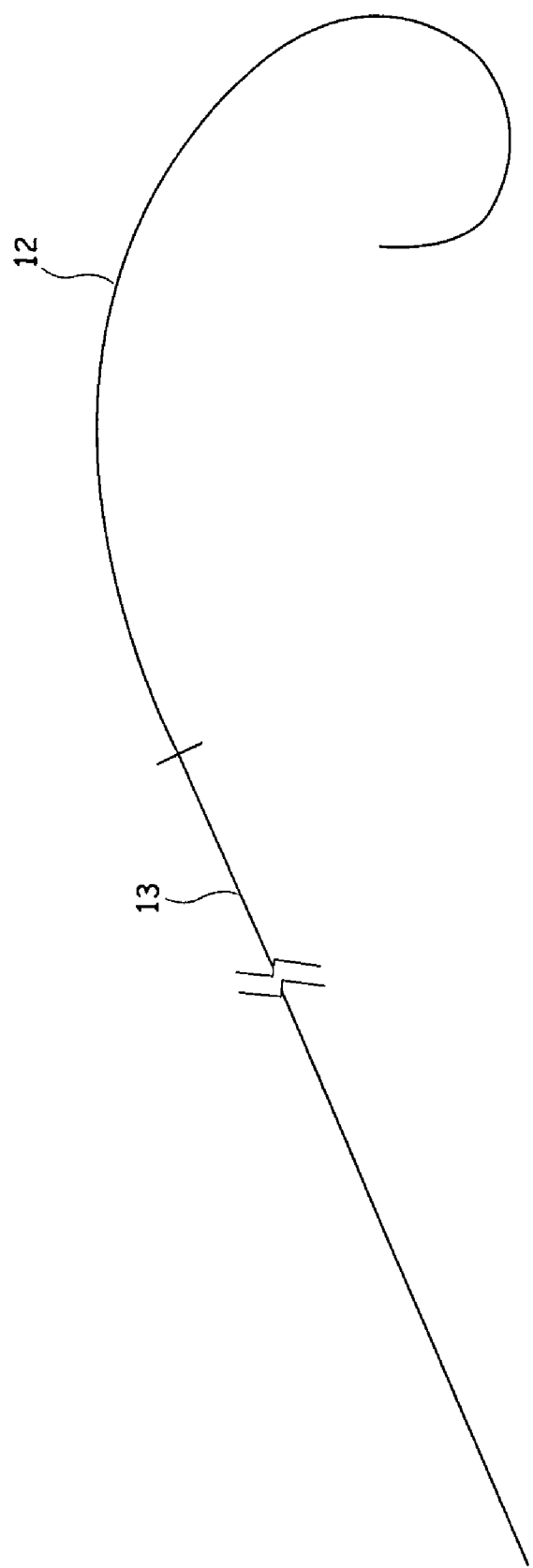
FIG. 2 is a schematic drawing of the guide wire of FIG. 1.
Figure 3:
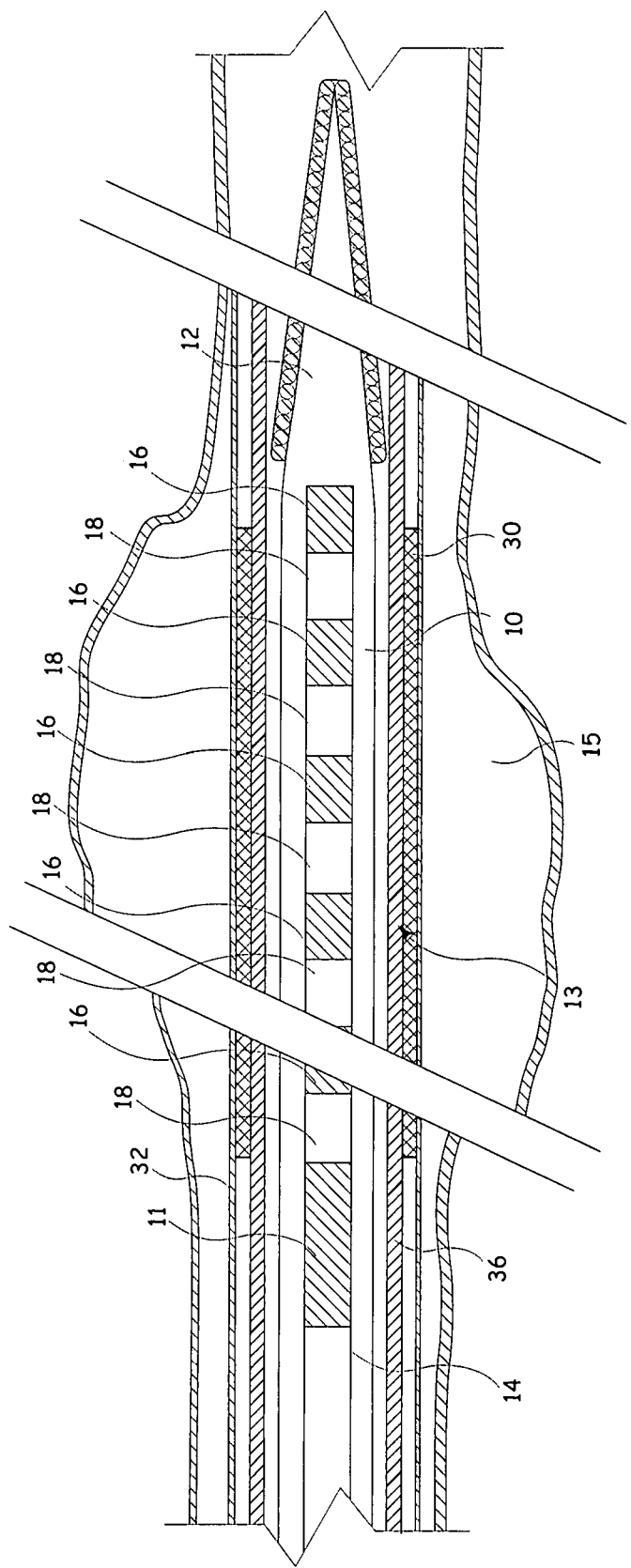
FIG. 3 shows the arrangement of the guide wire of FIG. 1 with a catheter.

The compressed granular sections 16, 18 cause the guide wire 10 to be relatively rigid at the portion just proximal to the flexible tip 12 (i.e. at the location of deployment of the implant), that is preferably to have a rigidity similar to that of existing guide wires. This is illustrated in FIG. 2, in which it can be seen that the tip 12 is flexible and thus able to negotiate a patient's vasculature easily. The dimensioning portion 13 is able to follow the tip 12 but still support a catheter 36 carrying an implant 30 thereon at the site of deployment and to remain substantially straight.

A stent 30 may be deployed in a biliary tract of a patient by first introducing the guide wire 10 through an access catheter across the distal segment of the target lesion 15 of the biliary tract. Once the guide wire 10 is in place, the patient is X-rayed in order to visualize the dimensioning portion of the guide wire 10. The surgeon or clinician is then able to use the 1 cm alternating radio-opaque zones 16 and radio-transparent zones 18 in order to measure the target lesion 15. An appropriate implant can then be selected. The introducer catheter on which the selected implant is mounted is fed over the guide wire 10 until the distal end of the introducer catheter is over the target lesion.

Once the introducer catheter has been located at the deployment site, the stent or other implant held by the device is ready to be deployed.

In order to deploy the stent 30, the introducer catheter 32 is retracted from the inner catheter 36 with the result that the stent 30 is exposed and allowed to expand gradually as the introducer catheter 32 moves backwards relative to the inner catheter 36. Once the stent 30 has been deployed, the delivery assembly can be withdrawn from a patient by pulling.

The guide wire 10 thus provides several advantages over existing guide wires. In particular, the step of using a separate dimensioning catheter in order to measure the site of treatment is rendered unnecessary. This thus reduces the number of components required and speeds up the process of deployment. Furthermore, the guide wire provides an additional locator for assisting in the correct positioning of the implant during the deployment step. By contrast, in prior art procedures, the dimensioning catheter must be removed prior to delivery of the introducer catheter carrying the implant and thus there is no positioning scale at the target site during deployment as there is with the system disclosed in this application.

An advantage of using a granular filler to form the alternating radio-opaque zones 16 and radio-transparent zones 18 is that this can be compressed until it forms a substantially rigid structure within the guide wire 10.

The skilled person will appreciate that modifications could be made. For example, instead of using a granular material, the lumen 14 of the guide wire 10 could be filled with alternating radio-opaque and radio-transparent rods, which are then compressed together longitudinally by a suitable bung 11. Compression of such markers can be achieved by hammering (swaging) a bung 11 into the proximal end of the guide wire lumen 14. This also has the effect of pushing the bung 11 against the marker material to compress it further and also against the internal walls of the sheath by swaging, thereby to create a unitary structure to gain stiffness. Swaging prevents movement of the sheath 32 with respect to the markers.

Alternatively, a single elongate element having bands of radio-opaque material could be used. However, this is less preferred as the radio-transparent materials of which the elongate element may be based are quite flexible and thus a guide wire 10 of very small diameter is likely to be insufficiently rigid for a number of medical applications.

Of course, the zones 16, 18 need not be 1 cm in length and could be of other lengths, for example from a few millimeters to 2 cm or more. However, zones of 1 cm will meet most medical needs.

It is advantageous that the lengths of either all of the radio-opaque zones 16 and/or all of the radio-transparent zones be the same, although in some embodiments the radio-opaque zones 16 and the radio-transparent zones 18 need not be the same length as one another. For example, a 2 mm radio-opaque zone 16 may separate radio-transparent zones of 1 cm. Other arrangements may be envisaged.

Moreover, although the preferred embodiments have been described in relation to the applicant's Zilver™ stent and delivery system, the teachings herein are applicable to all other catheter or cannula based delivery systems suitable for delivering stents, stent-grafts, filters, occlusion devices and other implants. For example, it could be used in the aorta.

What is claimed is:

1. A guide wire for a catheter, said guide wire having a longitudinal axis, wherein said guide wire includes a sheath; and wherein a plurality of marker elements is housed within a lumen of said sheath and regularly spaced along said longitudinal axis, said marker elements being separated from one another by spacer elements, the spacer elements being radio transparent, wherein said marker elements and spacer elements are formed by a granular material within said sheath.

2. The guide wire of claim 1, wherein said marker elements are formed by tungsten powder and said spacer elements are formed by sand.

3. The guide wire of claim 1, wherein said granular material is held in place by a bung.

4. The guide wire of claim 1, including at least two radio-opaque marker elements.

5. The guide wire of claim 4, wherein said at least two radio-opaque marker elements are separated by a known distance by a spacer element.

6. The guide wire of claim 5, wherein said distance is approximately 1 cm.

7. The guide wire of claim 6, wherein said at least two radio-opaque marker elements are approximately 1 cm in length.

8. The guide wire of claim 1, wherein the marker elements and spacer elements are formed from alternating radio-opaque and radio-transparent rods.

9. A delivery or treatment system including the guide wire of claim 1.

10. A guide wire for a catheter, said guide wire having a longitudinal axis, wherein said guide wire includes a sheath containing a granular material, wherein said granular material forms at least two radio-opaque markers, wherein said markers are regularly spaced along said longitudinal axis, said markers alternating with radio-transparent bands of granular material, and wherein said guide wire houses a bung, said bung holding said granular material in place.

11. A guide wire for a catheter, said guide wire having a longitudinal axis, wherein said guide wire includes a sheath; and wherein a plurality of marker elements separated by spacer elements is housed within said sheath, the marker elements being mere radio-opaque and said spacer elements being radio transparent, wherein said marker elements and spacer elements are formed by a granular material within said sheath and wherein said granular material is held in place by a bung.

* * * * *